(12) United States Patent
Mehlberg et al.

(10) Patent No.: US 8,889,076 B2
(45) Date of Patent: Nov. 18, 2014

(54) FLUID CATALYTIC CRACKING SYSTEM AND PROCESS

(75) Inventors: Robert L. Mehlberg, Wheaton, IL (US); Lawrence L. Upson, Barrington, IL (US); James P. Glavin, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 1027 days.

(21) Appl. No.: 12/344,598

(22) Filed: Dec. 29, 2008

(65) Prior Publication Data

US 2010/0168488 A1    Jul. 1, 2010

(51) Int. Cl.

| | |
|---|---|
| *B01J 8/26* | (2006.01) |
| *B01J 38/30* | (2006.01) |
| *C10G 51/00* | (2006.01) |
| *B01J 29/80* | (2006.01) |
| *C10G 51/06* | (2006.01) |
| *C10G 51/02* | (2006.01) |
| *B01J 29/90* | (2006.01) |
| *B01J 29/08* | (2006.01) |
| *B01J 29/40* | (2006.01) |

(52) U.S. Cl.
CPC .. *B01J 8/26* (2013.01); *B01J 38/30* (2013.01); *C10G 51/00* (2013.01); *B01J 29/80* (2013.01); *C10G 51/06* (2013.01); *C10G 51/026* (2013.01); *C10G 2300/1074* (2013.01); *C10G 2300/301* (2013.01); *B01J 29/084* (2013.01); *C10G 2400/20* (2013.01); *B01J 2208/025* (2013.01); *B01J 29/90* (2013.01); *C10G 2300/107* (2013.01); *B01J 29/40* (2013.01)
USPC ............ 422/141; 422/142; 422/144; 422/145

(58) Field of Classification Search
None
See application file for complete search history.

(56) References Cited

U.S. PATENT DOCUMENTS

| | | | |
|---|---|---|---|
| 3,470,084 A | 9/1969 | Scott | |
| 3,928,172 A * | 12/1975 | Davis et al. | ..................... 208/77 |
| 4,090,948 A | 5/1978 | Schwarzenbek | |
| 4,090,949 A | 5/1978 | Owen et al. | |
| 4,717,466 A | 1/1988 | Herbst et al. | |
| 4,830,728 A * | 5/1989 | Herbst et al. | ..................... 208/78 |
| 5,154,818 A | 10/1992 | Harandi et al. | |
| 5,314,610 A | 5/1994 | Gartside | |
| 5,346,613 A | 9/1994 | Lomas et al. | |

(Continued)

FOREIGN PATENT DOCUMENTS

| | | |
|---|---|---|
| CN | 1506342 A | 6/2004 |
| CN | 1506343 A | 6/2004 |

(Continued)

OTHER PUBLICATIONS

Abul-Hamayel et al., Enhancement of Propylene Production in a Downer FCC Operation Using a ZSM-5 Additive, Chemical Engineering & Technology, 2005, vol. 28(8), pp. 923-929.

(Continued)

*Primary Examiner* — Jennifer A Leung
(74) *Attorney, Agent, or Firm* — James C Paschall (57) ABSTRACT

One exemplary embodiment can be a fluid catalytic cracking system. Generally, the fluid catalytic cracking system includes a first reaction vessel and a second reaction vessel. The first reaction vessel may contain a first catalyst having pores with openings greater than about 0.7 nm and a second catalyst having pores with smaller openings than the first catalyst. What is more, the second reaction vessel may contain the second catalyst. Generally, at least a portion of the second catalyst is directly communicated with the first reaction vessel.

18 Claims, 4 Drawing Sheets

(56) References Cited

U.S. PATENT DOCUMENTS

| | | | |
|---|---|---|---|
| 5,372,704 | A | 12/1994 | Harandi et al. |
| 5,451,313 | A | 9/1995 | Wegerer et al. |
| 5,843,377 | A | 12/1998 | Fandel et al. |
| 5,846,403 | A | 12/1998 | Swan et al. |
| 5,981,819 | A | 11/1999 | Moeller et al. |
| 5,997,728 | A | 12/1999 | Adewuyi et al. |
| 6,093,867 | A | 7/2000 | Ladwig et al. |
| 6,106,697 | A | 8/2000 | Swan et al. |
| 6,222,087 | B1 | 4/2001 | Johnson et al. |
| 6,307,117 | B1 | 10/2001 | Tsunoda et al. |
| 6,388,152 | B1 | 5/2002 | Ladwig et al. |
| 6,444,868 | B1 | 9/2002 | Vaughn et al. |
| 6,455,750 | B1 | 9/2002 | Steffens et al. |
| 6,489,530 | B1 | 12/2002 | Stuntz |
| 6,646,175 | B1 | 11/2003 | Dath et al. |
| 6,646,176 | B1 | 11/2003 | Dath et al. |
| 6,791,002 | B1 | 9/2004 | Abrevaya et al. |
| 6,858,133 | B2 | 2/2005 | Dath et al. |
| 6,951,968 | B1 | 10/2005 | Dath et al. |
| 6,953,872 | B1 | 10/2005 | Koss et al. |
| 7,247,233 | B1 | 7/2007 | Hedrick et al. |
| 7,261,807 | B2 | 8/2007 | Henry et al. |
| 7,312,370 | B2 | 12/2007 | Pittman et al. |
| 2001/0044565 | A1 | 11/2001 | Keady et al. |
| 2002/0003103 | A1 | 1/2002 | Henry et al. |
| 2002/0189973 | A1 | 12/2002 | Henry et al. |
| 2003/0149322 | A1 | 8/2003 | Koss et al. |
| 2004/0112793 | A1 | 6/2004 | Dath et al. |
| 2004/0182747 | A1 | 9/2004 | Chen et al. |
| 2005/0150817 | A1 | 7/2005 | Tallman et al. |
| 2005/0234282 | A1 | 10/2005 | Bach et al. |
| 2006/0108261 | A1 | 5/2006 | Steffens et al. |
| 2006/0138027 | A1 | 6/2006 | Soni et al. |
| 2006/0260981 | A1 | 11/2006 | Gosling |
| 2006/0287561 | A1 | 12/2006 | Choi et al. |
| 2007/0038010 | A1 | 2/2007 | Xie et al. |
| 2007/0083071 | A1 | 4/2007 | Choi et al. |
| 2007/0205139 | A1 | 9/2007 | Kulprathipanja et al. |
| 2007/0246400 | A1 | 10/2007 | Jens et al. |
| 2007/0265482 | A1 | 11/2007 | Tsunoda et al. |
| 2008/0035527 | A1 | 2/2008 | Eng et al. |
| 2008/0093263 | A1 | 4/2008 | Cheng et al. |

FOREIGN PATENT DOCUMENTS

| | | |
|---|---|---|
| CN | 1600757 A | 3/2005 |
| CN | 1611472 A | 5/2005 |
| CN | 1676213 A | 10/2005 |
| CN | 1704389 A | 12/2005 |
| CN | 1762931 A | 4/2006 |
| CN | 1912065 A | 2/2007 |
| CN | 1915922 A | 2/2007 |
| CN | 1915924 A | 2/2007 |
| CN | 1915928 A | 2/2007 |
| CN | 1915929 A | 2/2007 |
| CN | 1915930 A | 2/2007 |
| CN | 1915935 A | 2/2007 |
| CN | 1927780 A | 3/2007 |
| CN | 1927783 A | 3/2007 |
| CN | 1962577 A | 5/2007 |
| CN | 1978410 A | 6/2007 |
| EP | 0 921 176 A1 | 6/1999 |
| WO | WO-2004/072002 A1 | 8/2004 |
| WO | WO-2007/135055 A1 | 11/2007 |
| WO | WO-2007/135058 A1 | 11/2007 |
| WO | WO 2008/008527 A2 | 1/2008 |

OTHER PUBLICATIONS

Buchanan et al., Effects of High Temperature and High ZSM-5 Additive Level on FCC Olefins Yields and Gasoline Composition, Applied Catalysis, A: General, 1996, vol. 134(2), pp. 247-262.

Chan et al., SCC Advanced FCCU Technology for Maximum Propylene Production, Hydrocarbon Asia, Oct. 1999, vol. 9/7, pp. 52-55.

Chan et al., SCC [(Selective Component Cracking)]: Advanced FCCU Technology for Maximum Propylene Production, AIChE 1999 Spring National Meeting, Preprint N. 40c, Mar. 1999, p. 7 pages.

Abstract of CN 1506342 published Jun. 23, 2004.
Abstract of CN 1506343 published Jun. 23, 2004.
Abstract of CN 1600757 published Mar. 30, 2005.
Abstract of CN 1611472 published May 4, 2005.
Abstract of CN 1676213 published Oct. 5, 2005.
Abstract of CN 1704389 published Dec. 7, 2005.
Abstract of CN 1762931 published Apr. 26, 2006.
Abstract of CN 1912065 published Feb. 14, 2007.
Abstract of CN 1915922 published Feb. 21, 2007.
Abstract of CN 1915924 published Feb. 21, 2007.
Abstract of CN 1915928 published Feb. 21, 2007.
Abstract of CN 1915929 published Feb. 21, 2007.
Abstract of CN 1915930 published Feb. 21, 2007.
Abstract of CN 1915935 published Feb. 21, 2007.
Abstract of CN 1927780 published Mar. 14, 2007.
Abstract of CN 1927783 published Mar. 14, 2007.
Abstract of CN 1962577 published May 16, 2007.
Abstract of CN 1978410 published Jun. 13, 2007.

Corma et al., Light Cracked Naphtha Processing: Controlling Chemistry for Maximum Propylene Production, Catalysis Today, 2005, vol. 107-108, pp. 699-706.

Fu et al., Using ZSM-5 Additive with DMS Based (Distributed Matrix Structure) FCC Catalyst for Increased Propylene Production, Preprints-American Chemical Society, Division of Petroleum Chemistry, 2006, vol. 51(2), pp. 588-589.

Hemler et al., Maximising FCC Propylene Production, Petroleum Technology Quarterly, Summer 1999, vol. 4, No. 2, pp. 31, 33-35.

Johnson et al., FCC Design for Maximum Olefin Production, NPRA 1993 Annual Meeting, vol. N.AM-93-51, pp. 1-27.

Lesemann et al., Increasing FCC Propylene, Petroleum Technology Quarterly, Jan./Feb./Mar. 2006, vol. 11/1, pp. 53-57.

Li et al., Highly Selective Conversion of Olefin Components in FCC Gasoline to Propylene in Monolithic Catalytic Reactors, China Petroleum Processing and Petrochemical Technology, 2006, No. (3), pp. 21-25.

Lomas et al., Improved Product Distributions Via Multiple Reaction Zones in Commercial FCC Units, 15th World Petroleum Congress Proceedings, 1998, vol. 2, pp. 728-729.

Lu et al., Exploratory Study on Upgrading 1-Butene Using Spent FCC Catalyst/Additive Under Simulated Conditions of FCCU's Stripper, Applied Catalysis, A: General, 2003 vol. 255(2), pp. 345-347.

Meng et al., Reducing FCC Gasoline Olefin and Enhancing Propylene Yield with FDFCC Process, World Petroleum Congress Proceedings, 2006, vol. 2006, p. 7.

Tallman et al., Special Report: Consider New Catalytic Routes for Olefins Production, Hydrocarbon Processing, Apr. 2008, vol. 87/4, pp. 95-96, 98, 100-101.

Verstraete et al., Study of Direct and Indirect Naphtha Recycling to a Resid FCC Unit for Maximum Propylene, Catalysis Today, 2005, vol. 106(1-4), pp. 62-71.

Wang et al., New FCC Process Minimizes Gasoline Olefin, Increases Propylene, Oil & Gas Journal, 2003, vol. 101(6), pp. 52-53, 56-58.

Ware et al., Special Focus [on] Catalysts/Maximizing Refinery Propylene Production Using ZSM-5 Technology, Fuel Technology & Management, May 1998, vol. 8, No. 4, pp. 41-46.

Abstract of WO/2004072002 published Aug. 26, 2004.

Yu et al., Commercial Practice on Technology for High-Temperature Cracking of C4 Fraction to Increase Propylene Yield, China Petroleum Processing and Petrochemical Technology, 2003, No. (3), pp. 29-32.

\* cited by examiner

FIG. 1

TARGET RISER OUTLET
TEMPERATURE, °C
— 521
-- 543
— 566

TARGET RISER RESIDENCE
TIME, SEC
□ 1.5
+ 2.5
× 3.5
= 4.5

FLUID CATALYTIC CRACKING SYSTEM AND PROCESS

FIELD OF THE INVENTION

This invention generally relates to a fluid catalytic cracking system and process for producing desired products, such as light olefins including propylene.

DESCRIPTION OF THE RELATED ART

Catalytic cracking can create a variety of products from larger hydrocarbons. Often, a feed of a heavier hydrocarbon, such as a vacuum gas oil, is provided to a catalytic cracking reactor, such as a fluid catalytic cracking reactor. Various products may be produced from such a system, including a gasoline product and/or light product such as propylene and/or ethylene.

In such systems, a single reactor or a dual reactor can be utilized. Although additional capital costs may be incurred by using a dual reactor system, one of the reactors can be operated to tailor conditions for maximizing products, such as light olefins including propylene and/or ethylene.

It can often be advantageous to maximize yield of a product in one of the reactors. Additionally, there may be a desire to maximize the production of a product from one reactor that can be recycled back to the other reactor to produce a desired product, such as propylene.

Moreover, some dual reactor systems utilize a mixture of catalysts, such as a larger pore catalyst and a smaller pore catalyst. In some instances, the mixture can be subject to regeneration. In such systems, the regeneration may have an adverse affect on catalyst performance. Particularly, some catalyst can require little or no regeneration. Hence, the common regeneration of the mixture may result in unnecessarily regenerating and possibly deactivating one of the catalysts of the mixture. Consequently, it typically would be beneficial to segregate the catalysts for controlling the regeneration thereof.

Thus, there can be a desire to provide a dual reactor system for catalytic cracking that may maximize operation conditions for producing one or more desired products.

SUMMARY OF THE INVENTION

One exemplary embodiment can be a fluid catalytic cracking system. Generally, the fluid catalytic cracking system includes a first reaction vessel and a second reaction vessel. The first reaction vessel may contain a first catalyst having pores with openings greater than about 0.7 nm and a second catalyst having pores with smaller openings than the first catalyst. What is more, the second reaction vessel may contain the second catalyst. Generally, at least a portion of the second catalyst is directly communicated with the first reaction vessel.

Another exemplary embodiment can be a fluid catalytic cracking system. The fluid catalytic cracking system can include a first reaction zone, a second reaction zone, and a regeneration zone. Generally, the first reaction zone operates at a conversion rate of no more than about 80%, by weight, based on a fresh feed for producing C3-C10 olefins. Typically, the second reaction zone receives another feed at least partially comprised of one or more C4-C10 olefins produced by the first reaction zone. The regeneration zone communicating with the first reaction zone may regenerate a catalyst from the first reaction zone.

A further exemplary embodiment may be a process for generating propylene in a system. The process may communicate a first reaction vessel with a regeneration zone and a second reaction vessel. Usually, the first reaction vessel contains a first catalyst having pores with openings greater than about 0.7 nm and a second catalyst having pores with smaller openings than the first catalyst. In addition, the second reaction vessel can contain only a catalytically effective amount of the second catalyst.

Thus, the embodiments disclosed herein can provide a dual reactor system that can maximize the production of a desired product, such as a light olefin, e.g., propylene. The embodiments disclosed herein can control conversion conditions by reducing the temperature and/or limiting the amount of catalyst in the reactor to reduce the conversion of the feed. The resultant product can be sent to a product separation zone that provides an olefinic recycle stream of one or more C4-C10 olefins. The olefinic recycle stream can be sent to another reaction zone for making a desired product, such as propylene. In addition, other embodiments as disclosed herein can provide a mechanism for isolating catalyst in one reaction zone from catalyst in another reaction zone. Particularly, the catalyst in a second reaction zone can be of one type and isolated from the other first reaction zone so, e.g., regenerated catalyst does not enter the second reaction zone. In such an instance, the second reaction zone can be communicated with the first reaction zone for providing a spent catalyst to the first reaction zone. Subsequently, the spent catalyst may be regenerated from the first reaction zone. The second reaction zone can receive fresh catalyst and only contain unregenerated catalyst to maintain a high conversion level for that zone for producing a desired light olefin product, such as propylene. Hence, the embodiments disclosed herein can provide a mechanism for maximizing a desired product yield, particularly a light olefin.

DEFINITIONS

As used herein, the term "fixed bed" generally means a catalyst that remains substantially stationary in a reactor.

As used herein, the term "fluidized bed" generally means that catalytic solids are suspended within the bed.

As used herein, the term "riser reactor" generally means a reactor used in a fluid catalytic cracking process that can include a riser, a reaction vessel, and a stripper. Usually, such a reactor may include providing catalyst at the bottom of a riser that proceeds to a reaction vessel having a mechanism for separating the catalyst from a hydrocarbon.

As used herein, the term "fresh feed" generally means a hydrocarbon provided to a reaction zone for conversion, where the hydrocarbon typically does not include one or more products from the reaction zone. Namely, the fresh feed does not include recycled products from that reaction zone whether they are directly recycled from a reaction zone outlet or provided from another zone, such as a product separation zone. However, the fresh feed can include hydrocarbons from other parts of a refinery or a petrochemical manufacturing facility that may be considered recycle streams within the refinery or facility.

DETAILED DESCRIPTION

Figure 1:
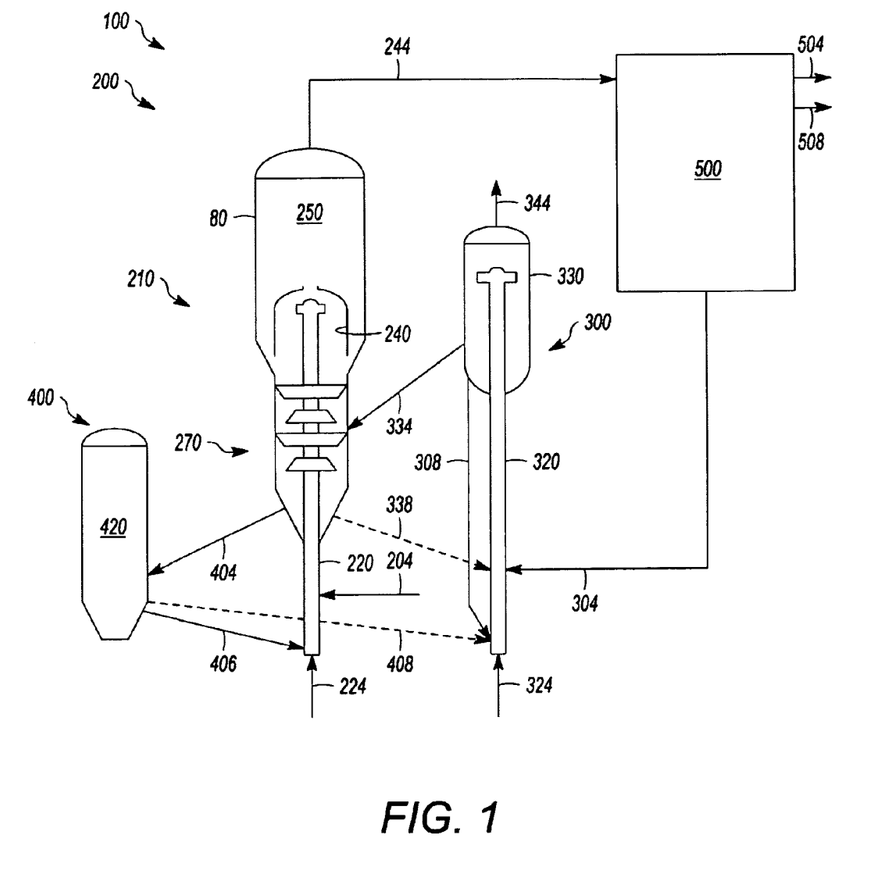
FIG. 1 is a schematic depiction of an exemplary system.

Referring to FIG. 1, a fluid catalytic cracking system 100 can include a first reaction zone 200, a second reaction zone 300, a regeneration zone 400, and a product separation zone 500. Generally, the first reaction zone 200 can include a riser reactor or riser reaction vessel 210. Although a riser reactor 210 is depicted, it should be understood that any suitable reactor or reaction vessel can be utilized, such as a fluidized bed reactor or a fixed bed reactor. Generally, the riser reactor 210 can include a first riser 220 terminating in a first reaction vessel 240. The first riser 220 can receive a feed 204 that can have a boiling point range of about 180-about 800° C. Typically, the feed 204 can be at least one of a gas oil, a vacuum gas oil, an atmospheric gas oil, and an atmospheric residue. Alternatively, the feed 204 can be at least one of a heavy cycle oil and a slurry oil. Generally, the feed 204 can be a fresh feed. As such, the feed 204 generally does not receive any recycled hydrocarbons from the first reaction zone 200. In an alternative embodiment, the feed 204 can receive a recycle stream from, for example, the product separation zone 500. It should be noted that process flow lines in the figures can be referred to interchangeably as, e.g., lines, pipes, conduits, feeds, mixtures or streams. Particularly, a line, a pipe, or a conduit can contain one or more feeds, mixtures, or streams, and one or more feeds, mixtures, or streams can be contained by a line, a pipe, or a conduit.

Generally, the feed 204 can be provided at any suitable height on the first riser 220, such as above a line 224 providing a lift gas, such as steam and/or a light hydrocarbon, to the riser 220. The feed 204 may be provided at a distance sufficient to provide a good dispersion of the up-flowing feed and/or catalyst, if desired. Although not depicted, a mixing chamber can also be provided at the bottom of the first riser 220 to mix, e.g., a mixture of spent and regenerated catalyst. An exemplary mixing chamber is disclosed in, e.g., U.S. Pat. No. 5,451,313.

The catalyst can be a single catalyst or a mixture of different catalysts. Usually, the catalyst includes two components or catalysts, namely a first component or catalyst, and a second component or catalyst. Such a catalyst mixture is disclosed in, e.g., U.S. Pat. No. 7,312,370 B2.

Generally, the first component may include any of the well-known catalysts that are used in the art of FCC, such as an active amorphous clay-type catalyst and/or a high activity, crystalline molecular sieve. Zeolites may be used as molecular sieves in FCC processes. Preferably, the first component includes a large pore zeolite, such as a Y-type zeolite, an active alumina material, a binder material, including either silica or alumina, and an inert filler such as kaolin.

Typically, the zeolitic molecular sieves appropriate for the first component have a large average pore size. Usually, molecular sieves with a large pore size have pores with openings of greater than about 0.7 nm in effective diameter defined by greater than about 10, and typically about 12, member rings. Pore Size Indices of large pores can be above about 31. Suitable large pore zeolite components may include synthetic zeolites such as X and Y zeolites, mordenite and faujasite. A portion of the first component, such as the zeolite, can have any suitable amount of a rare earth metal or rare earth metal oxide.

The second component may include a medium or smaller pore zeolite catalyst, such as a MFI zeolite, as exemplified by at least one of ZSM-5, ZSM-11, ZSM-12, ZSM-23, ZSM-35, ZSM-38, ZSM-48, and other similar materials. Other suitable medium or smaller pore zeolites include ferrierite, and erionite. Preferably, the second component has the medium or smaller pore zeolite dispersed on a matrix including a binder material such as silica or alumina and an inert filler material such as kaolin. The second component may also include some other active material such as Beta zeolite. These compositions may have a crystalline zeolite content of about 10-about 50 weight percent (hereinafter may be abbreviated as "wt. %") or more, and a matrix material content of about 50-about 90 wt. %. Components containing about 40 wt. % crystalline zeolite material are preferred, and those with greater crystalline zeolite content may be used. Generally, medium and smaller pore zeolites are characterized by having an effective pore opening diameter of less than or equal to about 0.7 nm, rings of about 10 or fewer members, and a Pore Size Index of less than about 31.

The total mixture in the first reaction zone 200 may contain about 1-about 25 wt. % of the second component, namely a medium to small pore crystalline zeolite with greater than or equal to about 1.75 wt. % of the second component being preferred. When the second component contains about 40 wt. % crystalline zeolite with the balance being a binder material, an inert filler, such as kaolin, and optionally an active alumina component, the mixture may contain about 4-about 40 wt. % of the second catalyst with a preferred content of at least about 7 wt. %. The first component may comprise the balance of the catalyst composition. In some preferred embodiments, the relative proportions of the first and second components in the mixture may not substantially vary throughout the FCC system 100. The high concentration of the medium or smaller pore zeolite as the second component of the catalyst mixture can improve selectivity to light olefins. In one exemplary embodiment, the second component can be a ZSM-5 zeolite and the mixture can include about 4-about 10% ZSM-5 zeolite excluding any other components, such as binder and/or filler.

Preferably, at least one of the first and/or second catalysts is an MFI zeolite having a silicon to aluminum ratio greater than about 15, preferably greater than about 75. In one exemplary embodiment, the silicon to aluminum ratio can be about 15:1-about 35:1.

Generally, the first feed 204 and the catalyst mixture can be provided proximate to the bottom of the first riser 220. Typically, the first riser 220 operates with dilute phase conditions above the point of feed injection with a density that is less than about 320 kg/m³. Generally, the first feed 204 is introduced into the first riser 220 by a nozzle. Usually, the first feed 204 has a temperature of about 140-about 320° C. Moreover, additional amounts of feed may also be introduced downstream of the initial feed point.

In addition, the first reaction zone 200 can be operated at low hydrocarbon partial pressure in one desired embodiment. Generally, a low hydrocarbon partial pressure can facilitate the production of light olefins. Accordingly, the first riser 220 pressure can be about 170-about 250 kPa with a hydrocarbon partial pressure of about 35-about 180 kPa, preferably about 70-about 140 kPa. A relatively low partial pressure for hydrocarbon may be achieved by using steam as a diluent, in the amount of about 10-about 55 wt. %, preferably about 15 wt. % of the feed. Other diluents, such as dry gas, can be used to reach equivalent hydrocarbon partial pressures.

The one or more hydrocarbons and catalyst rise to the reaction vessel 240 converting the first feed 204. Usually, the feed 204 reacts within the first riser 220 to form one or more products. The first riser 220 can operate at any suitable temperature, and typically operates at a temperature of about 150-about 580° C., preferably about 520-about 580° C. In one exemplary embodiment, a higher riser temperature may be desired, such as no less than about 565° C. In another exemplary embodiment as further discussed herein, it is desirable to control the conversion rate within the first riser 220 and the first reaction vessel 240. As a consequence, typically, the conversion is no more than about 80%, preferably no more than about 78%, and optimally no more than about 75%, by weight based on a fresh feed from producing C3-C10 olefins effective for maximizing subsequent production of olefins, such as propylene. In such an instance, possibly a lower riser temperature may be desired, such as no more than about 530° C. Alternatively, a lower catalyst activity can be provided to the first riser 220. Although not wanting to be bound by theory, a lower catalyst activity can limit hydrogen-transfer and hence constrain olefin saturation. Exemplary risers are disclosed in, e.g., U.S. Pat. Nos. 5,154,818 and 4,090,948.

The products can rise within the first riser 220 and exit within the first reaction vessel 240. Typically, products including propylene and gasoline are produced. Subsequently, the catalyst can separate assisted by any suitable device, such as swirl arms, and settle to the bottom of the first reaction vessel 240. In addition, a first mixture including one or more products and any remaining entrained catalyst can rise into a disengagement zone 250. In the disengagement zone 250, any remaining entrained catalysts can be separated. Generally, the first reaction zone 200 can include a shell 80 containing at least a portion of the reaction vessel 240, the disengagement zone 250, and optionally at least a portion of a stripping zone 270. Although the reaction vessel 240 is described as being a reaction vessel, it should be understood that other processes can occur such as the separation of catalysts from the hydrocarbons exiting the first riser 220. As such, reactions may primarily occur in the riser 220 that can be at least partially contained by and incorporated in the reaction vessel 240. Moreover, the reaction vessel 240 can include the stripping zone 270. Particularly, although catalyst is being separated from the hydrocarbons, some reactions may still occur within the first reaction vessel 240. Usually, the disengagement zone 250 can include separation devices, such as one or more cyclone separators for separating out the products from the catalyst particles. Dip legs can drop the catalyst down to the base of the shell 80 where openings can permit entry of the spent catalyst into the first reaction vessel 240 to a dense catalyst bed. Exemplary separation devices and swirl arms are disclosed in, e.g., U.S. Pat. No. 7,312,370 B2. The catalyst can pass through the stripping zone 270 where absorbed hydrocarbons can be removed from the surface of this catalyst by counter-current contact with steam. An exemplary stripping zone is disclosed in, e.g., U.S. Pat. No. 7,312,370 B2. Afterwards, the catalyst can be regenerated, as discussed below.

The one or more products leaving the disengagement zone 250 can exit as a product stream 244 to the product separation zone 500. Generally, the product separation zone 500 can receive the product stream 244 and other streams. Typically, the product separation zone 500 can include one or more distillation columns. Such zones are disclosed in, e.g., U.S. Pat. No. 3,470,084. Usually, the product separation zone 500 can produce several products. As an example, a propylene product can exit via a line 504, and a gasoline product can exit via a line 508. Particularly, various streams can be obtained depending on the columns in the product separation zone 500.

In addition, the product separation zone 500 can provide a feed 304, which can at least partially be comprised of C4-C10 olefins produced by the first reaction zone 200 and provided to the second reaction zone 300. Typically, the stream 304 can be provided above a line 324 providing a lift gas, such as steam and/or a light hydrocarbon, to the second riser 320. Optionally, the steam may be provided in the amount of about 5-about 40%, by weight, with respect to the weight of the feed 304. The stream 304 can include at least about 50%, by mole, of the components in a gas phase. Preferably, the entire stream 304, i.e., at least about 99%, by mole is in a gas phase. Generally, the temperature of the stream 304 can be about 120-about 600° C. when entering the second riser 320. Usually, the temperature of the stream 304 should at least be above the boiling point of the components. Otherwise, the feed can be provided directly to the riser with the catalyst recirculated from the reaction vessel 330.

The second reaction zone 300 can include a second riser 320 terminating in a second reaction vessel 330. In addition to the feed 304, catalyst may be recycled via a line 308 from the second reaction vessel 330. Optionally, as indicated by the dashed lines in FIG. 1, spent catalyst can be provided from the stripping zone 270 via a line 338 and/or the regeneration zone 400 via a line 408. In the latter, bringing catalyst from the regeneration zone 400 can provide additional heat to the second reaction zone 300. Usually, a chamber can be provided at the base of the second riser 320 that may receive catalyst. Such a mixing chamber is disclosed in, e.g., U.S. Pat. No. 5,451,313. Although the second reaction zone 300 is depicted as a riser reactor, it should be understood that any suitable reactor can be utilized, such as a fixed bed or a fluidized bed. In some embodiments, the second reaction vessel 330 can contain a mixture of the first and second components as described above.

In one preferred embodiment, the second reaction vessel 330 can contain less than about 20%, preferably about 5%, by weight, of the first component and at least 20% by weight, of the second component. In one preferred embodiments, the catalyst mixture can include at least 20% by weight of a ZSM-5 zeolite and less than 50%, preferably 5%, by weight of a Y-zeolite. In another preferred embodiment, the second reaction vessel 330 can contain only the second component, preferably a ZSM-5 zeolite, as the catalyst not including any impurities, such as remnants of other catalyst associated, e.g., with the feed 304. In other words, the second reaction vessel 330 may contain other objects, such as vessel supports, but only the second component as the catalyst. The second mixture, catalyst, or component can be provided directly to the reaction vessel 330 and periodically be dispensed through a line 334 to the stripping zone 270. The dispensed catalyst can combine with the first mixture and provide additional catalyst activity to the combination. From the stripping zone 270, the combination can be regenerated and/or sent back to the riser 320.

Usually, the second reaction zone 300 can be isolated from the regeneration zone 400 so that regenerated catalyst is only returned to the first reaction zone 200. Typically, the second reaction zone 300 does not receive regenerated catalyst from the regeneration zone 400. Rather, the regeneration zone 400 can communicate directly with the first reaction vessel 240 and does not directly communicate with the second reaction vessel 330. In this embodiment, the second component, by not being exposed to repeated regenerations, can help preserve the component's activity. Instead, the component can be added to the reaction zone 300 and spent catalyst can be provided via a line 334 to the first reaction zone 200. Thus, the first reaction vessel 240 can receive catalyst directly, i.e., spent and unregenerated catalyst, from the second reaction vessel 330. The second reaction zone 300 can receive fresh catalyst to further enhance the conversion of the C4-C10 olefin stream 304 entering the second reaction zone 300. The second component may not require as high of activity in the first reaction zone 200 as the second reaction zone 300 to produce the desired olefins. In addition, in some preferred embodiments, a lower conversion rate within the first reaction zone 200 is beneficial to produce C4-C10 olefins, which can in turn be converted to light olefins, such as ethylene and propylene in the second reaction zone 300.

The second riser 320 can operate in any suitable condition, such as a temperature of about 425-about 705° C., preferably a temperature of about 550-about 600° C., and a pressure of about 40-700 kPa, preferably a pressure of about 40-about 400 kPa, and optimally a pressure of about 200-about 250 kPa. Typically, the residence time of the second riser 320 can be less than about 3 seconds, preferably less than about 1 second, and optimally less than about 0.5 second. Exemplary risers and/or operating conditions are disclosed in, e.g., US 2008/0035527 A1 and U.S. Pat. No. 7,261,807 B2.

Generally, the stream 304 and the catalyst can rise to the second reaction vessel 330 and the catalyst and the hydrocarbon products can separate. The catalyst can drop to a dense catalyst bed within the second reaction vessel 330 and optionally be provided to the base of the second riser 320. Alternatively, spent catalyst can be periodically withdrawn from the second zone 300 via a conduit 334 to the first reaction zone 200 and replaced by fresh catalyst to maintain activity in the second reaction zone 300. Generally, the second reaction zone 300 may operate under conditions to convert the C4-C10 olefins into one or more light olefins, such as ethylene and/or propylene, preferably propylene. Afterwards, the hydrocarbon products can separate and exit the reaction zone 300 through a line 344.

The catalyst utilized in the first reaction zone 200 and the second reaction zone 300 can be separated from the hydrocarbons. As such, the catalysts can settle into the stripping zone 270 and be subjected to stripping the stream and subsequent regeneration. Next, the stripped catalyst via a conduit 404 can enter the regeneration zone 400, which can include a regeneration vessel 420. The regeneration vessel 420 can be operated at any suitable conditions, such as a temperature of about 600-about 800° C., and a pressure of about 160-about 650 kPa. Exemplary regeneration vessels are disclosed in, e.g., U.S. Pat. Nos. 7,312,370 B2 and 7,247,233 B1. Afterwards, the regenerated catalyst can be provided to the first riser 220 by the conduit 406 and optionally to the second riser 320 via the line 408.

Typically, the second reaction vessel 330 can be at least 50% smaller, preferably at least 60% smaller, than the first reaction vessel 240. In one desired embodiment, the catalyst in the second reaction vessel 330 can remain for any suitable time, typically, the time can be greater than about 20 days before being sent to the first reaction zone 200. Because the catalyst in the second reactor vessel 330 is a combination of fresh and variously aged catalysts, the transfer time between the first reaction vessel 240 and the second reaction vessel 330 can be possibly longer than 20 days. Generally, the longer the average age, the less the addition rate, and hence, less the daily catalyst cost. Thus, this provides additional savings to the second reaction vessel 330. Typically, it is desirable for the second reaction vessel 330 to contain only unregenerated catalyst to maintain the catalyst life. Particularly, the second catalyst component, e.g., ZSM-5, generally tends not to have great accumulation of coke, and therefore, may only need to be regenerated rarely, if at all. As such, typically the second reaction vessel 330 can contain an unregenerated catalyst. The second reaction zone 300 can be operated at a temperature greater than the first reaction zone 200, preferably a temperature of about 600-about 700° C. As discussed above, it is also possible to run the first reaction zone 200 to produce a large amount of C4-C10 olefins, which can be subsequently fed to the second reaction zone 300 for producing light olefins such as propylene.

Illustrative Embodiment(s)

The following examples are intended to further illustrate the subject. These illustrations are not meant to limit the claims to the particular details of these examples. These examples are based on engineering calculations and actual operating experience with similar processes.

The following example depicts data averages from a non-heat-balance pilot plant study on a hydrotreated feed blend of coker and virgin gas oils with a ZSM-5 catalyst system at different reaction times, temperatures, pressures, and catalyst/oil ratios. The catalyst is a coke-selective rare-earth commercially equilibrium catalyst with a ZSM-5 level optimized for maximum propylene production at 78-80 wt. % conversion in the presence of significant amounts of nickel, vanadium, and sodium in the fresh feed. A catalyst with improved lower gas and hydrogen selectivity and lower rare earth metal content can be used to increase olefin yield and increase conversion. The conversion of the total fresh feed is noted at the maximum yield of various olefin molecules as depicted in TABLE 1 below. As an example, the total yield of C3-C10 olefins is observed at a maximum of 29.5% based on fresh feed (abbreviated in FIGS. 2-4 as "FF 2") of which 11 wt. % is propylene. At this maximum yield, the conversion of the fresh feed is at 75 wt. %. In contrast, at a maximum propylene yield of 12.1 wt. %, the fresh feed conversion is 82 wt. %. However, the total C3-C10 olefin yield declines to 25.1 wt. %. Thus, the 1.1 wt. % increase in propylene and a 3.4% increase in ethylene associated with the increasing conversion from 75-82 wt. % can be accomplished with a 4.4 wt. % loss of the C3-C10 olefins. However, the C4-C10 olefins can be recycled and converted to propylene or ethylene in a second reaction zone. As a further comparison, the total C3-C10 olefins are nearly as high at 78 wt. % conversion, which can be heat balanced by conventional means for this catalyst and feed. A doubling of hydrogen and coke and a quadrupling of methane and ethane are also observed at conversions of 75.0 wt. % and 82.0 wt. %, as depicted below.

TABLE 1

(All Data In Units Of Wt. %)

| | | | |
|---|---|---|---|
| Conversion | 75.0 | 78.0 | 82.0 |
| C3-C10 Olefins | 29.5 | 28.5 | 25.1 |
| C3= | 11.0 | 11.7 | 12.1 |
| C2= | 1.7 | 2.5 | 5.1 |
| C1-C2 | 2.2 | 3.7 | 8.7 |
| Hydrogen | 0.19 | 0.24 | 0.38 |
| Coke | 3.4 | 4.8 | 7.3 |

Furthermore, the maximum C3-C10 total olefins occur at a coke yield of only 3.4 wt. %, which may be below that typically required for satisfying reaction heat balance requirements. A heavy cycle oil or slurry recycle can also be used to increase overall conversion and increase coke yield for heat balance requirements. Other variables for increasing olefin yield can include decreasing feed partial pressure, increasing riser temperature, and decreasing contact time.

Figure 2:
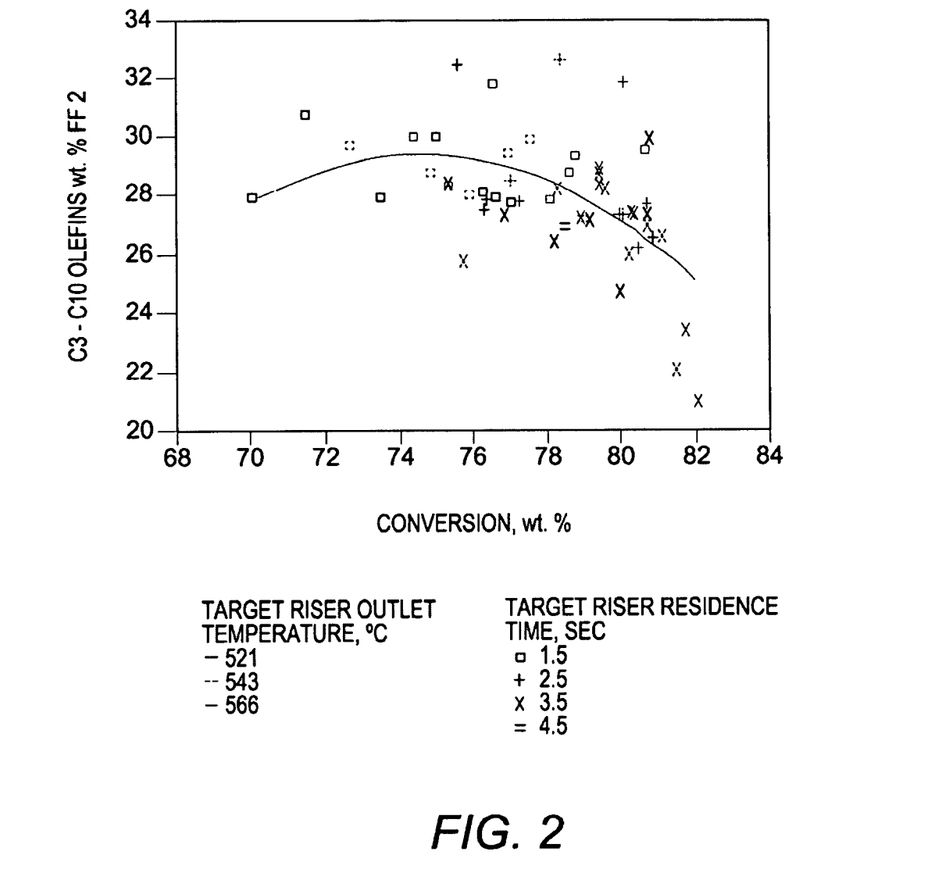
FIG. 2 is a graphical depiction of the yield of C3-C10 olefins versus conversion.
Figure 3:
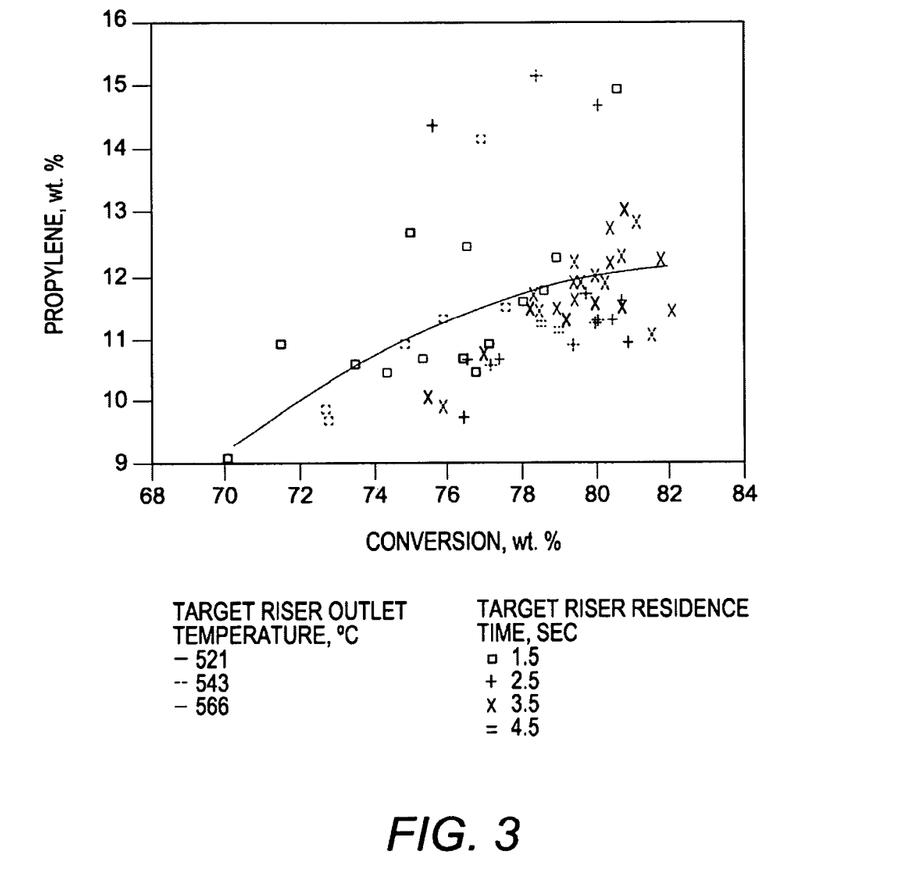
FIG. 3 is a graphical depiction of the yield of propylene versus conversion.
Figure 4:
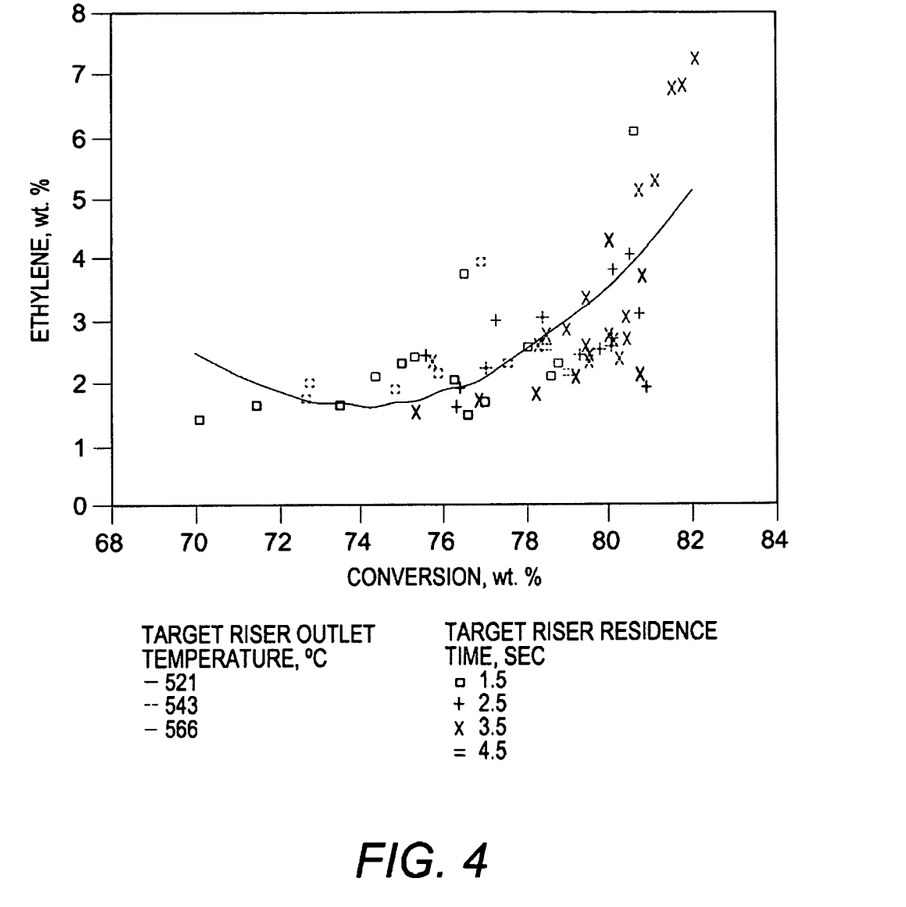
FIG. 4 is a graphical depiction of the yield of ethylene versus conversion.

Referring to FIGS. 2-4, simple regression models of yield versus conversion and conversion squared from process variables further illustrate the average yields. As depicted in FIG. 2, the total C3-C10 olefins go through a maximum of about 75 wt. % conversion for this catalyst and feed system before propylene yield reaches a maximum (as depicted in FIG. 3). Referring to FIG. 4, the ethylene yield also reaches a maximum at greater than 75 wt. % conversion. The curves represent the means of the data at each conversion limit and the upper and lower 95% confidence intervals for the mean. The yield shifts can be depicted by observing the quadratic model prediction profiles at 75 and 82 wt. % conversions. Thus, as depicted, it is illustrated that operating at a slightly lower conversion for propylene can increase the C4-C10 yield, which subsequently can be fed to a second reaction zone for increasing the overall system production of propylene.

Operating a fluid catalytic cracking process at lower conversion followed by separation and further reaction of the $C4^+$ olefin products in a second reaction zone can maximize the total yield and selectivity to propylene of the entire system at the expense of gas, hydrogen, and coke. Other variables, such as partial pressure temperature, riser residence time and/or catalyst/oil ratios may also increase olefin yield.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A fluid catalytic cracking system, comprising:
   A) a first reaction vessel containing a first catalyst having pores with openings greater than about 0.7 nm and a second catalyst having pores with smaller openings than the first catalyst and a first riser terminating in said first reaction vessel; and
   B) a second reaction vessel containing only the second catalyst for catalyzing at least one reaction wherein at least a portion of the second catalyst is directly communicated with the first reaction vessel through a line and a recycle line that recycles a second portion of the second catalyst to the second reaction vessel and a second riser terminating in said second reaction vessel.

2. The system according to claim 1, wherein the second catalyst comprises an MFI zeolite with a Si/Al ratio greater than about 15.

3. The system according to claim 1, further comprising a regeneration zone directly communicating with the first reaction vessel and not communicating directly with the second reaction vessel.

4. The system according to claim 1, wherein the second reaction vessel only contains an unregenerated second catalyst for catalyzing at least one reaction.

5. The system according to claim 1, wherein the second reaction vessel does not communicate with a regeneration zone to receive regenerated catalyst.

6. A fluid catalytic cracking system, comprising:
   A) a first reaction vessel containing a first catalyst having pores with openings greater than about 0.7 nm and a second catalyst having pores with smaller openings than the first catalyst and a first riser terminating in said first reaction vessel; and
   B) a second reaction vessel containing only an unregenerated catalyst wherein at least a portion of the unregenerated catalyst is directly communicated with the first reaction vessel through a line and a recycle line that recycles a second portion of the unregenerated catalyst to the second reaction vessel and a second riser terminating in said second reaction vessel.

7. The system according to claim 6, wherein the second reaction vessel only contains the second catalyst for catalyzing at least one reaction.

8. The system according to claim 6, wherein the second catalyst comprises an MFI zeolite with a Si/Al ratio greater than about 15.

9. The system according to claim 6, further comprising a regeneration zone directly communicating with the first reaction vessel and not communicating directly with the second reaction vessel.

10. The system according to claim 6, wherein the second reaction vessel does not communicate with a regeneration zone to receive regenerated catalyst.

11. The system according to claim 6, wherein the second reaction vessel contains less than about 20%, by weight, of the first catalyst and at least about 20%, by weight, of the second catalyst.

12. The system according to claim 6, wherein the second reaction vessel contains less than about 5%, by weight, of the first catalyst and at least about 20%, by weight, of the second catalyst.

13. A fluid catalytic cracking system, comprising:
   A) a first reaction vessel containing a first catalyst having pores with openings greater than about 0.7 nm and a second catalyst having pores with smaller openings than the first catalyst and a first riser terminating in said first reaction vessel;
   B) a second reaction vessel containing the second catalyst wherein at least a portion of the second catalyst is directly communicated with the first reaction vessel through a line and a recycle line that recycles a second portion of the second catalyst to the second reaction vessel; and a second riser terminating in said second reaction vessel; and
   C) a regeneration zone directly communicating with the first reaction vessel and not communicating directly with the second reaction vessel.

14. The system according to claim 13, wherein the second reaction vessel only contains the second catalyst for catalyzing at least one reaction.

15. The system according to claim 13, wherein the second catalyst comprises an MFI zeolite with a Si/Al ratio greater than about 15.

16. The system according to claim 13, wherein the second reaction vessel only contains an unregenerated second catalyst for catalyzing at least one reaction.

17. The system according to claim 13, wherein the second reaction vessel does not communicate with a regeneration zone to receive regenerated catalyst.

18. The system according to claim 13, wherein the second reaction vessel contains less than about 20%, by weight, of the first catalyst and at least about 20%, by weight, of the second catalyst.

* * * * *